United States Patent
Hess et al.

(10) Patent No.: US 10,520,427 B2
(45) Date of Patent: Dec. 31, 2019

(54) METHOD AND DEVICE FOR EVALUATING THE QUALITY OF A COMPONENT PRODUCED BY MEANS OF AN ADDITIVE LASER SINTERING AND/OR LASER MELTING METHOD

(71) Applicant: MTU Aero Engines AG, Munich (DE)

(72) Inventors: Thomas Hess, Munich (DE); Gunter Zenzinger, Waakirchen (DE); Wilhelm Satzger, Munich (DE)

(73) Assignee: MTU Aero Engines AG, Munich (DE)

(*) Notice: Subject to any disclaimer, the term of this patent is extended or adjusted under 35 U.S.C. 154(b) by 302 days.

(21) Appl. No.: 14/771,573

(22) PCT Filed: Feb. 27, 2014

(86) PCT No.: PCT/DE2014/000078
§ 371 (c)(1),
(2) Date: Aug. 31, 2015

(87) PCT Pub. No.: WO2014/135141
PCT Pub. Date: Sep. 12, 2014

(65) Prior Publication Data
US 2016/0018320 A1    Jan. 21, 2016

(30) Foreign Application Priority Data
Mar. 6, 2013 (DE) .................. 10 2013 003 760

(51) Int. Cl.
*G01J 5/00* (2006.01)
*G01N 21/27* (2006.01)
(Continued)

(52) U.S. Cl.
CPC ........... *G01N 21/27* (2013.01); *B22F 3/1055* (2013.01); *B29C 64/153* (2017.08); *G01N 21/35* (2013.01);
(Continued)

(58) Field of Classification Search
CPC ................................... G01J 2005/0077
(Continued)

(56) References Cited

U.S. PATENT DOCUMENTS 5,225,883 A * 7/1993 Carter ............... F23N 5/085
356/45
6,489,801 B1  12/2002 Borden et al.
(Continued)

FOREIGN PATENT DOCUMENTS

DE    10004049        8/2000
DE    10004049 A1 *  8/2000 ............ G01N 25/72
(Continued)

OTHER PUBLICATIONS

Ian Gibson and Ling Wai Ming: Low-cost Machine Vision Monitoring of the SLS Process, pp. 59-66, XP002727082, Jul. 11, 2014.
(Continued)

*Primary Examiner* — Min Huang
(74) *Attorney, Agent, or Firm* — Barlow, Josephs & Holmes, Ltd.

(57) ABSTRACT

A method for evaluating the quality of a component produced by means of an additive laser sintering and/or laser melting method, in particular a component for an aircraft engine comprises at least the steps of providing a first data set, which comprises spatially resolved color values, which each characterize the temperature of the component at an associated component location during the laser sintering and/or laser melting of the component, providing a second data set, which comprises spatially resolved color values corresponding to the first data set, which color values each characterize the temperature of a reference component at an associated reference component location during the laser sintering and/or laser melting of the reference component.

9 Claims, 3 Drawing Sheets

(51) Int. Cl.
  *B29C 64/153* (2017.01)
  *B22F 3/105* (2006.01)
  *G01N 21/35* (2014.01)
  *B33Y 10/00* (2015.01)
  *B33Y 30/00* (2015.01)
  *B33Y 40/00* (2015.01)
  *G01N 21/17* (2006.01)

(52) U.S. Cl.
  CPC ....... *B22F 2003/1057* (2013.01); *B33Y 10/00* (2014.12); *B33Y 30/00* (2014.12); *B33Y 40/00* (2014.12); *G01N 2021/1765* (2013.01)

(58) Field of Classification Search
  USPC .......................................................... 367/124
  See application file for complete search history.

(56) References Cited

U.S. PATENT DOCUMENTS

| | | | |
|---|---|---|---|
| 6,758,595 B2 * | 7/2004 | Seitz | G01J 3/36 |
| | | | 348/E5.09 |
| 7,515,986 B2 | 4/2009 | Huskamp | |
| 7,640,125 B2 | 12/2009 | D'Angelo et al. | |
| 8,471,207 B2 * | 6/2013 | Louban | G01N 25/72 |
| | | | 250/341.6 |
| 2002/0111770 A1 * | 8/2002 | Kalvin | G01J 3/46 |
| | | | 702/183 |
| 2004/0026389 A1 | 2/2004 | Kessler et al. | |
| 2004/0026807 A1 | 2/2004 | Andersson et al. | |
| 2006/0032840 A1 | 2/2006 | Bagavath-Singh | |
| 2008/0262659 A1 | 10/2008 | Huskamp | |
| 2009/0206065 A1 | 8/2009 | Kruth et al. | |
| 2010/0118137 A1 | 5/2010 | Avila et al. | |
| 2010/0224772 A1 * | 9/2010 | Lemieux | G01D 18/008 |
| | | | 250/252.1 |
| 2011/0001809 A1 * | 1/2011 | McManus | G01J 5/02 |
| | | | 348/61 |
| 2011/0255847 A1 * | 10/2011 | Ji | H01L 21/67115 |
| | | | 392/407 |
| 2012/0038763 A1 * | 2/2012 | Kawada | B23B 25/06 |
| | | | 348/95 |
| 2014/0042137 A1 * | 2/2014 | Daniel | B23K 9/0953 |
| | | | 219/130.5 |
| 2014/0262124 A1 * | 9/2014 | Vilaro | B22D 19/00 |
| | | | 164/494 |
| 2014/0265047 A1 * | 9/2014 | Burris | B23K 26/034 |
| | | | 264/497 |
| 2015/0129581 A1 * | 5/2015 | Cole | B23K 9/0286 |
| | | | 219/60 A |
| 2016/0347005 A1 * | 12/2016 | Miller | B29C 67/0051 |
| 2017/0182562 A1 * | 6/2017 | Das | B22F 7/062 |

FOREIGN PATENT DOCUMENTS

| | | |
|---|---|---|
| DE | 10 2004 017 769 B4 | 12/2004 |
| DE | 102011009624 | 8/2012 |
| EP | 1134565 A1 | 9/2001 |
| EP | 1466718 A2 | 10/2004 |
| EP | 2271073 A2 | 1/2011 |
| EP | 2771073 A2 | 9/2014 |
| EP | 2771140 A2 | 9/2014 |
| EP | 2917797 A2 | 9/2015 |
| RU | 2386517 C1 * | 4/2010 |
| WO | 9805949 | 2/1998 |
| WO | 2007147221 A1 | 12/2007 |
| WO | 2009003702 A1 | 1/2009 |
| WO | 2012019577 A1 | 2/2012 |
| WO | 2012100766 A1 | 8/2012 |
| WO | 2013060981 A2 | 5/2013 |
| WO | 2014074947 A2 | 5/2014 |

OTHER PUBLICATIONS

Radovan Hudak et al: "Material and Thermal Analysis of Laser Sintered Products", XP055128301, pp. 15-19, Acta Mechanica, Bd. 7, Nr. 1, 1, Jan. 1, 2013.

Krauss, H & Eschey, C & Zaeh, M.F.. (Aug. 22, 2012). Thermography for monitoring the selective laser melting process. 23rd Annual International Solid Freeform Fabrication Symposium—An Additive Manufacturing Conference, SFF 2012. 999-1014.

* cited by examiner

METHOD AND DEVICE FOR EVALUATING THE QUALITY OF A COMPONENT PRODUCED BY MEANS OF AN ADDITIVE LASER SINTERING AND/OR LASER MELTING METHOD

BACKGROUND OF THE INVENTION

The invention relates to a method for evaluating the quality of a component produced by means of an additive laser sintering and/or laser melting method, in particular a component for an aircraft engine. The invention further relates to a device for carrying out a method of this type.

Additive laser sintering and laser melting methods for the manufacture of components, such as, for example, components for aircraft engines, are already known as such from DE 10 2004 017 769 B4, for example. In selective laser melting, thin layers of powder of the material or materials used are placed on a construction platform and locally melted and solidified by using one or a plurality of laser beams. The construction platform is then lowered and another layer of powder is applied and again locally solidified. This cycle is repeated until the finished component is obtained. The finished component can then be further processed as needed or immediately used. In selective laser sintering, the component is produced in a similar way by laser-assisted sintering of powdered materials. However, laser sintering and melting methods have not been used so far for serial production of components for aircraft engines. In addition, a process authorization, a prerequisite of which is the monitoring of diverse process parameters, such as, for example, the laser power as well as the nature and state of the powdered material and the like, is required, in particular, for the use of components that are produced by additive laser methods and are subject to high loads. In this case, the individual process parameters have to be monitored at intervals in the course of a process monitoring by means of a respectively adapted, elaborate method of measurement. The inspection effort that thereby ensues is great and correspondingly time-consuming and cost-intensive. Furthermore, a continuous monitoring of all relevant process parameters is often not possible a priori. In addition, all individual measurements must be harmonized with their respective tolerance ranges, as a result of which the analysis effort is additionally relatively great in order to be able to make statements about the quality of the component produced by additive manufacturing.

BRIEF SUMMARY OF THE INVENTION

The object of the present invention is to create a method for evaluating the quality of a component produced by means of an additive laser sintering and/or laser melting method, said method enabling an improved evaluation of the quality of the produced component. Another object of the invention is to create a suitable device for carrying out such a method.

The objects are achieved in accordance with the invention by a method as well as by a device. Advantageous embodiments with appropriate enhancements of the invention are discussed in detail below, in which advantageous embodiments of the method are to be regarded as advantageous embodiments of the device and vice versa.

A method according to the invention for evaluating the quality of a component produced by means of an additive laser sintering and/or laser melting method comprises the steps of providing a first data set, which comprises spatially resolved color values, which each characterize the temperature of the component at an associated component location during the laser sintering and/or laser melting of the component, providing a second data set, which comprises spatially resolved color values corresponding to the first data set, said color values each characterizing the temperature of a reference component at an associated reference component location during the laser sintering and/or laser melting of the reference component, determining a difference between the first data set and the second data set, and evaluating the quality of the component on the basis of the difference between the first data set and the second data set. In other words, it is provided in accordance with the invention that a first data set is provided, which, for at least certain positions of the component, includes a color value that characterizes a temperature at this position during the manufacture of the component. The component and the reference component, which may also be referred to as the master part, can be, for example, a component for an aircraft engine. For quality evaluation, these color values (or temperature values) are recorded in the course of a component authorization or acceptance based on a reference component and stored in a second data set, which is then provided for evaluating the quality of an analogously produced component. All components that are subsequently produced can thus be monitored simply and at will in real time by comparing the color value distribution of the respectively produced component to the corresponding color values of the master part for the component coordinates considered. In this way, any differences between the authorized reference component and the currently produced component can be determined and employed for evaluating the quality of the component, thereby enabling an especially simple, rapid, and cost-effective quality evaluation of the laser-sintered component. In addition, by systematically recording fluctuations of typical process variables, it is also possible to draw conclusions about all relevant process parameters and defects by means of only one comparison of data. The data sets can comprise, for example, data tuples of the form [x, y, z, color value], where x, y, and z are the component coordinates or global coordinates of a Cartesian coordinate system, for example. It is fundamentally possible also to be able to provide other suitable data structures. When the first data set and the second data set exist in different data structures, a data transformation can be provided for determining any difference between the two data sets. It is fundamentally also possible to provide that the first and/or second data set comprise or comprises additional measured values, metadata, etc., besides color values of the component or of the reference component that characterize the temperature. For example, the first and/or second data set can additionally comprise color values that characterize the temperature outside of the component, such as, for example, temperatures within a construction chamber in which the component is produced.

In an advantageous embodiment of the invention, it is provided that the method is carried out one time or multiple times during the additive laser sintering and/or laser melting of the component and/or for at least one line element of the component and/or for at least one surface area element of the component and/or for at least one volume element of the component and/or for the entire component and/or subsequent to the additive laser sintering and/or laser melting of the component. By carrying out the method at least one time during the manufacture of the component, it is possible to detect directly any unallowed structural deviations from the reference component and, depending on the deviation, to correct them already during manufacture. If, already during the manufacture of the component, an unallowed and irreparable deviation is detected, the finishing of the component can advantageously be dispensed with, thereby avoiding unnecessary losses in time and material. The difference between the component and the reference component can be determined in this process fundamentally along a line element, that is, along a desired trajectory through the component, with respect to a surface area element, that is, with respect to a sectional plane through the component, and/or for a volume element of the component. The analysis can occur layer by layer during, for example, the buildup of class 2 or higher-class components for aircraft engines. In the case of components that are less critical to safety, one analysis over the entire component may also be sufficient.

In another advantageous embodiment of the invention, it is provided that, on the basis of the determined difference, at least one other parameter is determined from the group composed of powder consumption, powder condition, laser power, uniformity of powder deposition, layer thickness, travel path of a construction platform used for laser sintering and/or laser melting, strip overlap, irradiation parameters, transferability of the laser sintering and/or laser melting method to a type of laser sintering and/or laser melting equipment that differs from the type of laser sintering and/or laser melting equipment used for the manufacture of the reference component, aging phenomena of the laser sintering and/or laser melting equipment used, and machine drift of the laser sintering and/or laser melting equipment used. In this way, it is possible advantageously to determine further information relevant to the manufacture in the course of evaluating the quality of the component and, as needed, to use this information to optimize the process.

In another advantageous embodiment of the invention, it is provided that the first data set and/or the second data set comprise(s) at least 1 million and preferably at least 2 million spatially resolved color values. In this way, especially reliable statements are made possible statistically. For example, the first data set and/or the second data set can comprise 1.0 million, 1.5 million, 2.0 million, 2.5 million, 3.0 million, 3.5 million, 4.0 million, 4.5 million, 5.0 million, 5.5 million, 6.0 million, 6.5 million, 7.0 million, 7.5 million, 8.0 million, 8.5 million, 9.0 million, 9.5 million, 10.0 million, or more spatially resolved color values.

Further advantages ensue when the first data set and/or the second data set are/is created from measured values that are determined by using at least one high-resolution detector and/or an optical thermography method. This permits an especially simple, precise, and cost-effective determination of the energy input and a correspondingly simple, precise, and cost-effective creation of the respective data set. Moreover, it is possible in this way to evaluate the quality of the component in an especially precise manner, because, for example, nonuniformities in the material, in the layer thickness, or in the heat input can be determined in an especially precise manner and can be stored in the form of a corresponding data set.

In another advantageous embodiment of the invention, it is provided that gray-scale values are used as color values for the first data set and/or for the second data set. In the context of the invention, gray-scale values refer to gradations between pure white and pure black. Because gray-scale values represent brightness values, it is possible in this way to achieve an especially simple and rapid analysis of the corresponding data set and a corresponding simple and rapid evaluation of the quality of the component. Gray-scale values can be deposited in the respective data set as values between 0 and 255, for example, or in hexadecimal notation, as values between #00 and #FF. It is fundamentally possible also to provide coarser or finer gradations of the gray-scale value.

Further advantages ensue when the difference between the first data set and the second data set is determined by using at least one histogram of the component and at least one corresponding histogram of the reference component and/or by using a cross correlation of the first and second data sets and/or by using an autocorrelation of the first data set and/or the second data set and/or by using a breakdown of the first and/or second data set into harmonic components and/or by using a determination of at least one line center of gravity and/or at least one surface area center of gravity and/or a volume center of gravity of the component and/or of the reference component. In this way, the method can be adapted optimally to the respective circumstances and can be carried out in a correspondingly rapid, simple, and precise manner. Moreover, a simple possibility is created in this way to perform a specific analysis of the component quality depending on whether different color or gray-scale values occur in large regions of one or a plurality of successive layers of the component or whether different color or gray-scale values occur in smaller regions or one or a plurality of successive layers of the component.

In another advantageous embodiment of the invention, it is provided that too low an energy input in the laser sintering and/or laser melting process and/or a drop in laser power and/or a contamination of an optical system of the laser sintering and/or laser melting equipment are/is concluded when at least one color value at a component location of the component is darker than a color value at a corresponding reference component location of the reference component. In this way, it is possible to make well-grounded inferences about possible manufacturing problems and method flaws, so that, by way of corresponding interventions in the laser sintering and/or laser melting process, the proportion of defective components can be at least significantly reduced or even completely prevented.

Accordingly, in a further advantageous embodiment of the invention, it is provided that too high an energy input in the laser sintering and/or laser melting process and/or too high a laser power and/or a poor heat conduction in the sintered material powder and/or a wrong material and/or a contaminated material and/or an aged material are/is concluded when at least one color value at a component location of the component is brighter than a color value at a corresponding reference component location of the reference component.

In another advantageous embodiment of the invention, it is provided that the component is classified as acceptable when the determined difference lies within predetermined limits or that the component is classified as not acceptable when the determined difference exceeds the predetermined limits. In this way, it is possible in an especially simple manner to distinguish between acceptable or allowed components and defective components.

A second aspect of the invention relates to a device for carrying out a method according to one of the preceding exemplary embodiments. Said device according to the invention comprises at least one additive laser sintering and/or laser melting equipment unit for manufacturing a component, in particular a component for an aircraft engine, a detection device, which is designed to record spatially resolved color values, which each characterize the temperature of the component at an associated component location during laser sintering and/or laser melting of the component, and a computing device. Said computing device is designed to generate a first data set from the spatially resolved color values and to provide a second data set, with the second data set comprising spatially resolved color values corresponding to the first data set, said color values each characterizing the temperature of a reference component at an associated reference component location during laser sintering and/or laser melting of the reference component. Furthermore, the computing device is designed to determine any difference between the first data set and the second data set and to evaluate at least the quality of the component on the basis of the difference between the first data set and the second data set. In this way, an especially rapid, simple, and detailed check and evaluation of the finished quality of the component is made possible. Further ensuing advantages may be taken from the preceding descriptions of the first aspect of the invention, whereby advantageous embodiments of the first aspect of the invention are to be regarded as advantageous embodiments of the second aspect of the invention and vice versa.

In an advantageous embodiment of the invention, it is provided that the detection device comprises at least one high-resolution detector and/or at least one IR-sensitive detector, in particular a CMOS and/or sCMOS and/or CCD camera, for recording IR radiation. Detectors and cameras of the types of design mentioned are capable of replacing most available CCD image sensors. In comparison to the previous generations of CCD-based sensors and cameras, cameras based on CMOS and sCMOS sensors offer various advantages, such as, for example, a very low readout noise, a high image rate, a large dynamic range, a high quantum efficiency, a high resolution, and a large sensor area. After creation of the data set, this then enables an especially good quality inspection of the manufactured component.

BRIEF DESCRIPTION OF THE DRAWINGS

Further features of the invention ensue from the claims and the exemplary embodiments as well as on the basis of the drawings. The features and combinations of features mentioned above in the description as well as the features and combinations of features mentioned below in the exemplary embodiments can be used not only in the respectively given combinations, but also in other combinations without departing from the scope of the invention.

Shown here are.

DETAILED DESCRIPTION OF THE INVENTION

Figure 1:
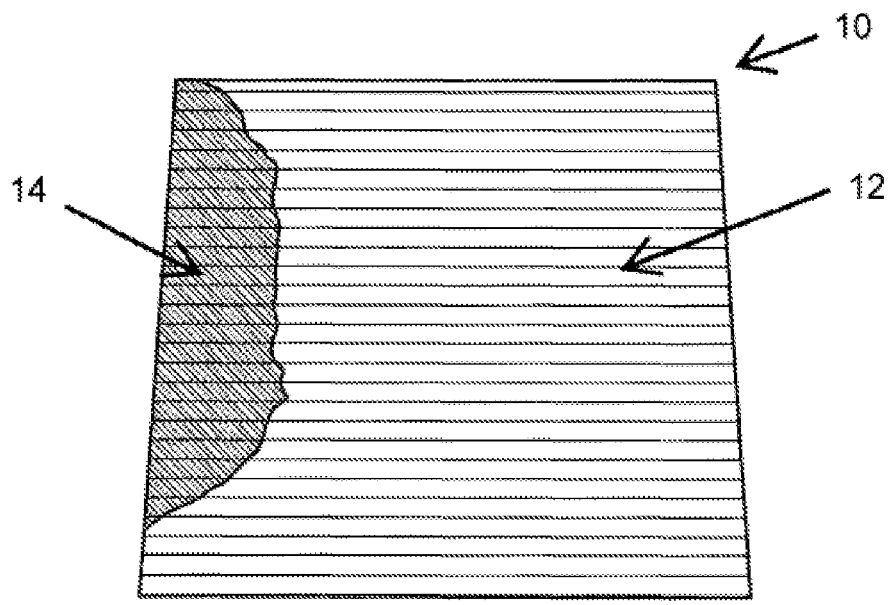
FIG. 1 a thermographic plan view of an additively manufactured layer of a component, which has regions with different temperatures.

FIG. 1 shows a thermographic plan view of a layer of a component 10 for an aircraft engine, said component 10 being manufactured from a corresponding material powder by using an additive laser sintering or laser welding method, which is known as such. On the one hand, a large-area region 12, which has a uniform temperature distribution, and, on the other hand, a smaller region 14, which, in comparison to the region 12, has a lower temperature, can be seen. The cross strips of the region 12 symbolize, in addition, a direction of layering during the additive manufacturing of the component 10. The temperatures are characterized in this case on the basis of spatially resolved gray-scale values, so that the region 14 appears darker than the region 12. The temperature values can be determined by thermographic methods and compiled in a first data set for each measured component coordinate, for example. In the process, the number of data points can be optimally adjusted depending on the respective manufacturing method and/or component.

The cause of the lower temperatures in the region 14 is primarily a deficient powder deposition. Too small a power deposition in the region 14 leads to a correspondingly more rapid emission of heat and to correspondingly lower surface temperatures, which are characterized by lower gray-scale values. Further causes can be too low an energy input in the region 14, owing to a drop in laser power, for example, a contamination of deflecting mirrors of the optical system, or the like. Vice versa, too high an energy input in the laser sintering and/or laser melting process, too high a laser power, too poor a heat conduction in the sintered material powder, an incorrect material, a contaminated material, and/or an aged material can be concluded when color or gray-scale values in one component region are markedly brighter than in other component regions.

Figure 2:
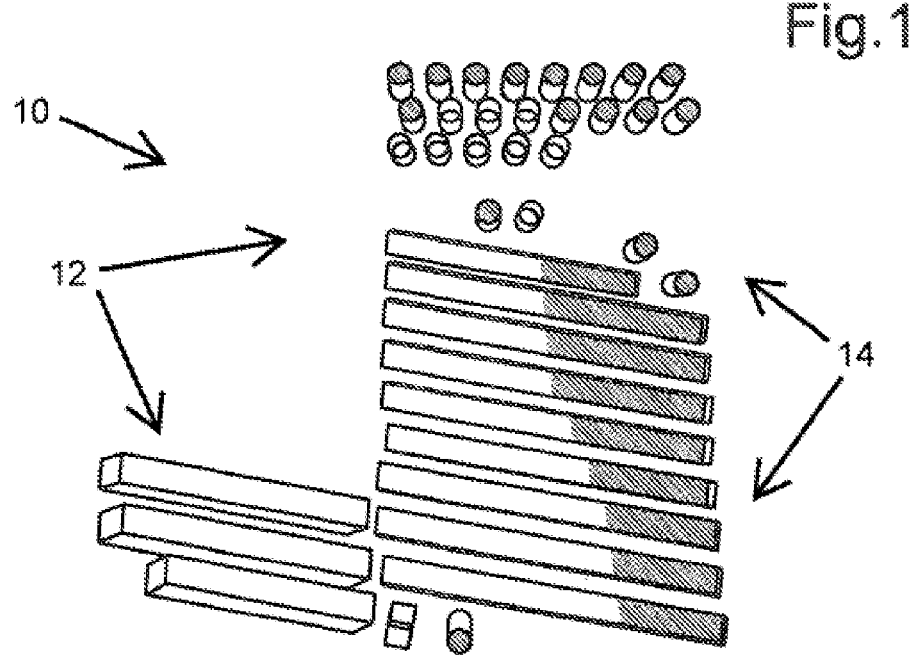
FIG. 2 a schematic plan view of a plurality of additively manufactured components with different temperature distributions.

FIG. 2 shows a schematic plan view of a plurality of jointly additively manufactured components 10 with different temperature distributions. Various brighter regions 12, which, correspondingly, have comparably higher temperatures, as well as various darker regions 14, which, correspondingly, have lower temperatures, can once again be seen. The cause of the different temperature distribution in the present example is a flow of gas passing downward from above in the construction chamber of laser sintering equipment used for manufacturing the components 10, said flow of gas leading locally to a greater cooling effect and thus an accumulation of comparatively colder component regions 14.

In order to be able to perform a reliable quality evaluation and, for example, to make a reliable decision as to whether the regions 12 are too bright or the regions 14 are too dark, the first data set of the component or components 10 is compared to a second, corresponding data set of a reference component or a master part.

Figure 3:
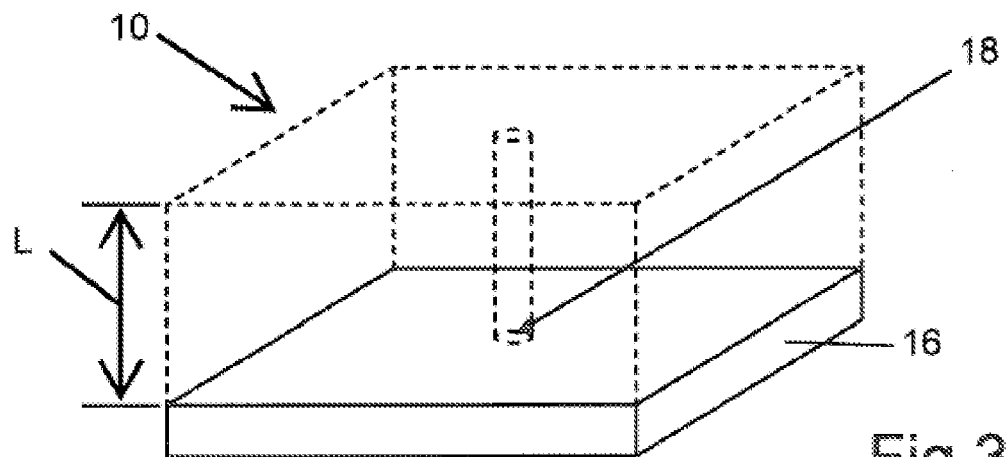
FIG. 3 a schematic perspective view of a component, in which a quality evaluation is carried out within a volume element.

For this purpose, FIG. 3 schematically shows a perspective view of a component 10, which was additively manufactured on a construction platform 16. The quality evaluation of the component 10, which, for simplicity, is depicted as being cube-shaped and has an edge length L, is carried out locally within a volume element 18 of the component 10. For this purpose, a first data set is provided, which comprises spatially resolved color or gray-scale values, which each characterize the temperature of the component 10 at an associated component location within the volume element 18 during laser sintering. Furthermore, a second data set is provided, which also comprises spatially resolved color or gray-scale values, which each characterize the temperature of a reference component within a corresponding volume element 18 during laser sintering and or laser melting of the reference component. An evaluation of the quality of the component 10 can be performed by determining one or a plurality of differences between the first data set and the second data set.

Figure 4:
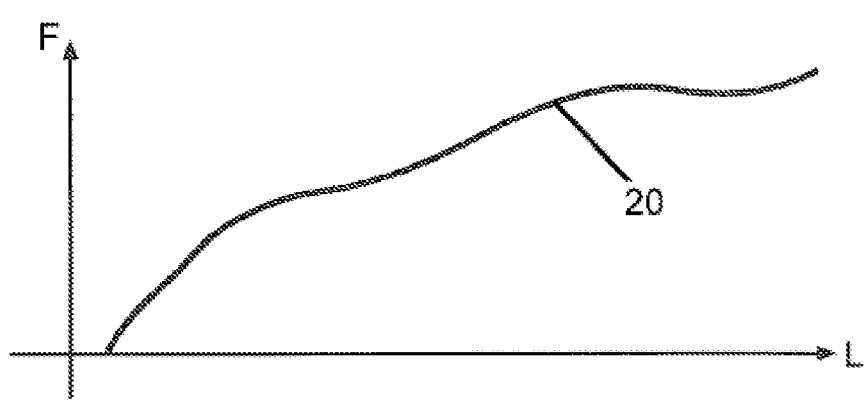
FIG. 4 a histogram of a reference component.

FIG. 4 shows a histogram 20 of a reference component (not shown) in the viewed volume element 18, in which color or gray-scale values F are plotted on the ordinate axis and the corresponding spatial coordinate L between the construction platform 16 and the top side of the component 10 is plotted on the abscissa axis. The histogram 20 thus describes the target-value brightness or target-value temperature curve within the volume element 18.

Figure 5:
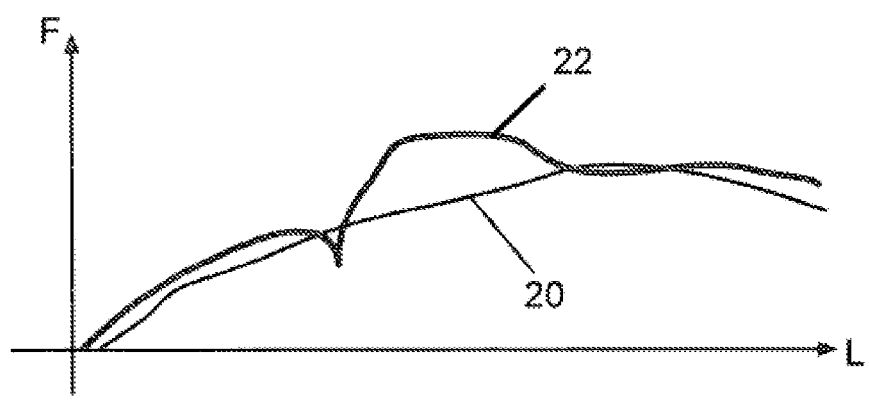
FIG. 5 an overlap of a histogram of a component with a corresponding histogram of the reference component.

FIG. 5 shows an overlap of a histogram 22 of a component 10 in the viewed volume element 18 with a corresponding histogram 20 of the reference component. Various spatially dependent temperature deviations can be seen. The differences in the spatially resolved temperature values can be determined, for example, by using a comparison between the histograms 20 and 22, by means of a cross correlation of the first and second data set of the volume element 18, by using an autocorrelation of the first data set and/or the second data set(s), by means of a breakdown of the first and/or the second data set(s) into harmonic components, and/or by using a determination of a volume center of gravity of the component 10 and of the reference component. If the differences exceed a predetermined limit value, the component 10 is classified as being not acceptable. If, by contrast, the differences lie within a predetermined tolerance range, the component 10 complies with the reference component and thus with the predetermined specifications.

Figure 6:
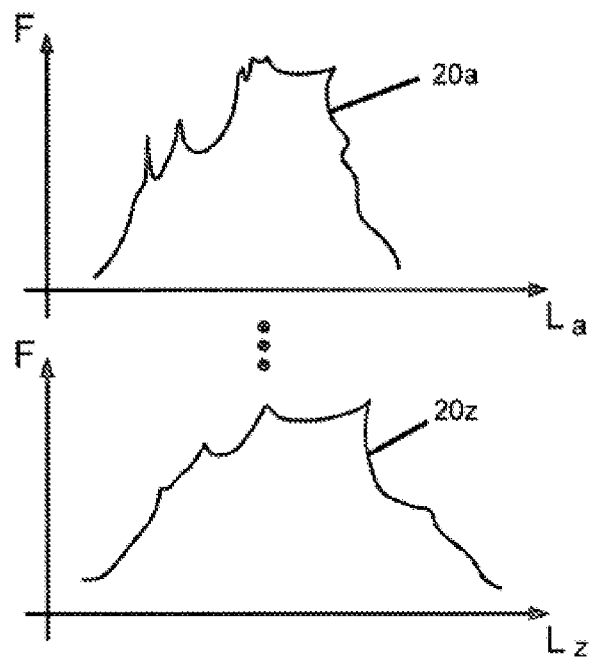
FIG. 6 a schematically indicated cluster of histograms of the reference component.
Figure 7:
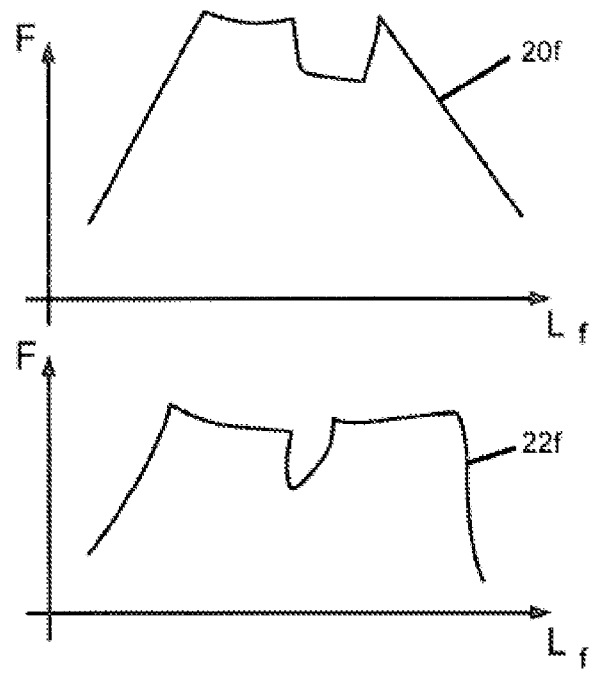
FIG. 7 a schematic comparison between a histogram of the reference component and an associated histogram of a component for evaluating the quality of the component.

FIG. 6 shows a schematically indicated cluster of histograms 20a to 20z along a corresponding cluster of lines La to Lz through the reference component, which serve for global analysis of the component quality, that is, for evaluation of the entire component 10. As is clear from FIG. 7, a comparison between each of the histograms 20a to 20z (here, histogram 20f by way of example) of the reference component and an associated histogram 22a to 22z (here, histogram 22f by way of example) of the component 10 are taken for evaluation of the component quality and, on the basis of any differences between the component 10 and the master, it is decided whether the component 10 complies or does not comply with the required specifications.

The parameter values given in the documents for definition of process and measurement conditions for the characterization of specific properties of the subject of the invention are to be regarded as also being in the scope of the invention within the context of deviations—for example, owing to measurement errors, system errors, weighing errors, DIN tolerances, and the like.

The invention claimed is:

1. A method for evaluating the quality of a component produced by an additive laser sintering and/or laser melting method, in real time, comprising the steps of:
    providing a construction platform;
    providing an additive laser manufacturing device including a laser;
    providing a powdered material on the construction platform;
    melting the powdered material with the laser;
    solidifying the powdered material into a layer of a machine component to be manufactured on the construction platform at an associated component location of the machine component by the additive laser manufacturing device;
        providing a thermographic capture device including a high-resolution camera configured and arranged for capturing IR radiation;
    capturing an image of the layer by the thermographic capture device;
    obtaining a first data set, from the image captured by the thermographic capture device, which comprises spatially resolved color values, which each characterize the temperature of the component at the associated component location during the laser sintering and/or laser melting of the machine component;
    providing a second data set, which comprises a second set of spatially resolved color values corresponding to the first data set, said second set of spatially resolved color values each characterizing the temperature of a reference component at an associated reference component location during a laser sintering and/or a laser melting of the reference component;
    comparing the first data set from the captured images from the machine component with the second data set of the values associated with the referenced component;
    determining a difference between the first data set and the second data set by:
        a comparison between at least one histogram of the component and at least one corresponding histogram of the reference component;
        a cross correlation of the first and second data sets;
        an autocorrelation of the first data set and/or the second data set;
        a breakdown of the first and/or the second data set into harmonic components; and
        a determination of at least one line center of gravity and/or at least one surface area center of gravity and/or a volume center of gravity of the component and/or of the reference component;
    setting a value for the maximum acceptable difference between the first data set and the second data set;
    evaluating the quality of the component on the basis of the difference between the first data set and the second data set;
    if the difference between the first data set and the second data set does not exceed the value for the maximum acceptable difference, a further layer of the machine component is formed; and
    if the difference between the first data set and the second data set exceeds the value for the maximum acceptable difference, the machine component is discarded,
    wherein the first data set or the second data set comprise at least 1 million spatially resolved color values.

2. The method according to claim 1, wherein,
on the basis of the determined difference, at least one other parameter is determined from the group composed of powder consumption, powder condition, laser power, uniformity of powder deposition, layer thickness, travel path of a construction platform used for laser sintering and/or laser melting, strip overlap, irradiation parameters, transferability of the laser sintering and/or laser melting method to a type of laser sintering and/or laser melting equipment that differs from the type of laser sintering and/or laser melting equipment used for manufacture of the reference component, aging phenomena of the laser sintering and/or laser melting equipment used, and machine drift of the laser sintering and/or laser melting equipment used.

3. The method according to claim 1, wherein
the first data set or the second data set comprise at least 2 million spatially resolved color values.

4. The method according to claim 1, wherein
the first data set and/or the second data set are/is created from measured values that are determined by using a high-resolution detector and/or an optical thermography method.

5. The method according to claim 1, wherein
gray-scale values are used as color values for the first data set and/or for the second data set.

6. The method according to claim 1, wherein
too low an energy input in the laser sintering and/or laser melting process and/or a drop in laser power and/or a contamination of an optical system of the laser sintering and/or laser melting equipment are/is concluded when at least one color value at a component location of the component is darker than a color value at a corresponding reference component location of the reference component.

7. The method according to claim 1, wherein
too high an energy input in the laser sintering and/or laser melting process and/or too high a laser power and/or a poor heat conduction in the sintered material powder and/or an incorrect material and/or a contaminated material and/or an aged material are/is concluded when at least one color value at a component location of the component is brighter than a color value at a corresponding reference component location of the reference component.

8. The method according to claim 1, wherein
the component is classified as being acceptable when the determined difference lies within predetermined limits, or in that the component is classified as being not acceptable when the determined difference exceeds the predetermined limits.

9. The method according to claim 1, wherein the detection device is selected from the group consisting of a CMOS camera, sCMOS camera and a CCD camera.

* * * * *